United States Patent [19]

Buchner et al.

[11] Patent Number: 5,278,054

[45] Date of Patent: Jan. 11, 1994

[54] PROCESS FOR THE ENZYMATIC HYDROLYSIS OF A CARBOXYLIC ACID DERIVATIVE

[75] Inventors: Maria Buchner; Robert Estermann, both of Linz; Herbert Mayrhofer, Engerwitzdorf; Gerald Banko, Linz, all of Austria

[73] Assignee: Chemie Linz Gesellschaft m.b.H., Linz, Austria

[21] Appl. No.: 870,429

[22] Filed: Apr. 17, 1992

[30] Foreign Application Priority Data

Apr. 29, 1991 [AT] Austria ...................... 886/91

[51] Int. Cl.$^5$ .................. C12P 7/02; C12P 7/40; C12P 7/62; C12P 41/00

[52] U.S. Cl. ...................... 435/136; 435/128; 435/130; 435/135; 435/141; 435/156; 435/180; 435/195; 435/196; 435/197; 435/198; 435/280

[58] Field of Search ............ 435/135, 136, 280, 180, 435/128, 130, 156, 141, 195, 196, 197, 198

[56] References Cited

U.S. PATENT DOCUMENTS

| | | | |
|---|---|---|---|
| 4,668,628 | 5/1987 | Dahod et al. | 435/136 |
| 4,800,162 | 1/1989 | Matson | 435/136 |
| 5,032,523 | 7/1991 | Amano et al. | 435/280 |
| 5,057,427 | 10/1991 | Wald et al. | 435/280 |
| 5,108,916 | 4/1992 | Cobb et al. | 435/135 |

FOREIGN PATENT DOCUMENTS 0206436 12/1986 European Pat. Off.
0257716 3/1988 European Pat. Off.

OTHER PUBLICATIONS

Biotech AN-90-01013 Akita et al Chem. Pharm. Bull (1989) 37, 10, 2867-78.
Biotech. AN-90-01027 (J01228964) Sep. 12, 1988.
Biotech. AN-86-03313 (J60248200) Dec. 7, 1985.
Biotech AN-14086 (J02190195) Jul. 26, 1990.
"Pakistan Journal of Biochemistry", 10(2) 41-53 (1976).
Chemical Abstracts, vol. 112, col. 154387z (1990).
Chemical Abstracts, vol. 109, col. 188832u (1988).

*Primary Examiner*—Herbert J. Lilling
*Attorney, Agent, or Firm*—Wenderoth, Lind & Ponack

[57] ABSTRACT

A process for the enzymatic hydrolysis of a carboxylic acid derivative by dissolving the carboxylic acid derivative in an organic solvent which is miscible with water only to a slight extent, saturation of the organic solution with water, bringing the water-saturated organic solution into contact with a hydrolase, the hydrolysis taking place, after which the reaction solution is saturated with water again and brought into contact with the hydrolase and subsequently with water again until the desired degree of conversion is achieved.

11 Claims, No Drawings

PROCESS FOR THE ENZYMATIC HYDROLYSIS OF A CARBOXYLIC ACID DERIVATIVE

The invention relates to a process for the enzymatic hydrolysis of a carboxylic acid derivative in an organic solvent.

A large number of enzymes are capable of hydrolyzing carboxylic acid derivatives more or less specifically. This property of hydrolases has been economically utilised for a long time. It is to be taken into account here that hydrolases normally exhibit good conversion rates and, in general, low activity losses in aqueous solutions, but that they are soluble in water and only rarely can be recovered from aqueous reaction solutions and employed again. Covalently immobilized hydrolases can indeed be recovered from aqueous solutions, but they have lower conversion rates and poorer activities than an identical amount of hydrolase which is employed in non-immobilized form. Additionally, enzyme is also always dissolved out of enzyme immobilizates in aqueous systems.

It has therefore already been attempted to carry out enzymatic hydrolyses in organic medium. Thus, in Pakistan Journal of Biochemistry, Vol. 10, No. 2, 1976, it is disclosed that during the hydrolysis of carboxylic acid esters the initial rate of hydrolysis in organic medium can sometimes be higher than in aqueous medium, but the activity of the hydrolase decreases rapidly in the organic medium, since hydrolases are sensitive to organic solvents. In Chemical Abstracts Vol. 112, 154387z, it is therefore proposed to chemically modify hydrolases in order to increase their tolerance to organic solvents. In Chemical Abstracts Vol. 109, 188832n, an enzymatic hydrolysis using a chemically modified hydrolase in water-saturated benzene is described.

It has now unexpectedly been found that it is not necessary for good conversion rates and constantly high activity of a hydrolase in an organic solvent to chemically modify the hydrolase if an organic solvent is used that is only miscible with water to a slight extent and if care is taken that the organic solvent remains saturated with water in the course of the hydrolysis, during which water is consumed.

The invention therefore relates to a process for the enzymatic hydrolysis of a carboxylic acid derivative, which is characterized in that the carboxylic acid derivative is dissolved in an organic solvent which is miscible with water only to a slight extent, after which the solution is saturated with water and brought into contact with a hydrolase, hydrolysis taking place with consumption of water, after which the organic reaction solution is saturated with water again and brought into contact with the hydrolase until the desired degree of conversion is achieved.

The process according to the invention is suitable for the hydrolysis of carboxylic acid derivatives which can be enzymatically hydrolyzed with the aid of a hydrolase. Such carboxylic acid derivatives are, for example, carboxylic acid esters, diesters, triesters, carboxylic acid amides, carboxylic acid thioesters etc. or analogous thiocarboxylic acid derivatives thereof. Particular importance is attached to the process for the hydrolysis of carboxylic acid derivatives which carry substituents in the acid moiety or in the derivative moiety which produces a chiral center in the molecule or of carboxylic acid derivatives in which a chiral center is formed as a result of the hydrolysis. Such chiral or prochiral carboxylic acid derivatives can be hydrolyzed with the aid of a stereospecific hydrolase to optically active compounds in which one of the possible enantiomers, depending on the stereospecificity of the hydrolase, is present in at least enriched form, chiral carboxylic acid derivatives being understood to mean both racemic mixtures and mixtures in which one of the possible enantiomers is present in at least enriched form.

Preferably, carboxylic acid derivatives are understood to mean mixtures of enantiomeric chiral carboxylic acid esters which have the chiral center in the acid moiety, particularly preferably 2-substituted alkanoic acid esters, very particularly preferably 2-halopropionic acid esters.

The hydrolysis products formed are accordingly carboxylic acids or thiocarboxylic acids and alcohols, amines, thiols etc., where either the carboxylic acids or the alcohols, amines, thiols, etc. or alternatively both are intended as the desired reaction products and can be recovered.

To carry out the process according to the invention, a carboxylic acid derivative is first dissolved in an organic solvent which is miscible with water only to a slight extent. Organic solvents used are, for example, hydrocarbons, such as pentane, hexane, benzene, toluene, halogenated hydrocarbons, such as methylene chloride, chloroform, carbon tetrachloride, ethylene chloride, chlorobenzenes, or ethers, such as diethyl ether, diisopropyl ether, or mixtures of such solvents. Preferred solvents are ethers, in particular diisopropyl ether. The selection of the solvent here can be important, since the reaction can proceed more rapidly in a certain solvent than in another. Under certain circumstances, it can be advantageous to add to the organic solvent a small amount of an organic co-solvent which is miscible with water, such as, for example, an alcohol, for example methanol, ethanol or isopropanol, a ketone, for example acetone etc., in order to increase the solubility of the carboxylic acid derivative in the organic solvent. The amount of the co-solvent added, however, must be so low that the organic solvent is not completely miscible with water as a result of addition of the co-solvent. The solvent for a desired conversion can easily be found by the person skilled in the art by simple preliminary experiments. The solution of the starting compound in the organic solvent is prepared as concentrated as possible, the concentration of the starting material in the solvent being dependent on the respective starting material and on the solvent used in each case.

The organic solution is then saturated with water. For saturation with water, the solution is either brought into contact with a system which contains bound water and which is capable of giving off this water on contact with an organic solvent, or with an aqueous phase. Systems which contain bound water are, for example, water-containing hydrogels, for example polyacrylamide gels, polysaccharide gels etc. An amount of bound water is added to the organic solution which suffices to saturate the solution with water, water being understood to mean pure water and buffer or salt solutions. The amount of the hydrogels used depends here on the water absorption capacity both of the hydrogel and of the organic solvent.

A suitable aqueous phase is pure water, a buffer solution or alternatively an aqueous salt solution. The buffer solution employed is expediently one of those in which the hydrolase exhibits high conversion rates and high specificity. For saturation with water, the organic solution is introduced directly into the aqueous phase or mixed with an aqueous phase and allowed to settle, 2 phases being formed.

The water-saturated solution is subsequently brought into contact with a hydrolase. Depending on the starting compound and the desired product, possible hydrolases are suitable hydrolases for the respective reaction. Examples of hydrolases are esterases, proteases, amidases etc. Expediently, depending on the desired reaction, a hydrolase is employed which carries out the reaction as specifically as possible, in the case of chiral or prochiral carboxylic acid derivatives as stereospecifically as possible. Preferably, a lipase is used in the process according to the invention. An advantage of the process according to the invention is that the hydrolase does not have to be chemically modified to increase its tolerance to chemical solvents. However, chemically modified hydrolases can also be employed in the process according to the invention. The hydrolases can be employed as such, adsorbed on a support, for example on Celite, silica gel, dust, glass beads or alternatively in immobilized form. Preferably, the hydrolase is employed adsorbed on an inert support, particularly preferably on Celite, it being sufficient for adsorption of the hydrolase on Celite simply to mix the hydrolase with Celite. A substantial advantage of the process is that the hydrolase does not have to be introduced in immobilized form, since it is insoluble in organic solvents.

If a water-containing hydrogel is used for saturating the organic solution with water, the hydrolase is added directly to the water-saturated solution in which the hydrogel is also present. On contact of the water-saturated solution with the hydrolase, the hydrolysis takes place to the enzyme-specific extent and with enzyme-specific selectivity, the water consumed during the hydrolysis being made up from the hydrogel so that the organic reaction solution always remains water-saturated. If a chiral or prochiral carboxylic acid derivative is employed, the reaction is allowed to proceed up to a desired degree of conversion which can be ascertained by determination of the optical rotation. After the desired degree of conversion has been achieved, the enzyme and the hydrogel are filtered off. Depending on the desired product, the solution can then be worked up in the customary manner, it being possible to obtain and/or purify the desired product with the aid of extraction, recrystallization, distillation or chromatography.

If an aqueous phase is used to saturate the organic solution with water, the hydrolase is introduced into a reaction container, for example into a column, and the water-saturated, organic solution is pumped through the container and over the hydrolase so that the hydrolase does not come into contact with the aqueous phase.

On contact of the organic water-saturated solution with the hydrolase, the hydrolysis takes place to an enzyme-specific extent and with enzyme-specific stereoselectivity. In this process, the water-saturated solution is passed continuously over the hydrolase and then through the aqueous phase, since the desired degree of conversion cannot in general be achieved on single contact of the hydrolase with the reaction solution. Since hydrolases in general are able to react with both enantiomers of an optically active carboxylic acid derivative, where, however, they preferably react with one enantiomer, it is in general appropriate in the case of chiral or prochiral carboxylic acid derivatives to measure the optical rotation of the reaction solution, which is a measure of the respective enantiomeric excess, continuously and to discontinue the reaction after conversion of the enantiomer preferred by the hydrolase, in order to obtain products which are as enantiomerically pure as possible.

During the continuous pumping of the organic, water-saturated solution over the enzyme, it is to be taken into account that the solution is always water-saturated on contact with the enzyme. Since one mol of water is consumed during the hydrolysis per mol of cleaved bond, this water must be replaced before the organic solvent again comes into contact with the hydrolase.

The water consumed can be replaced, for example, by passing the organic solution after contact with the hydrolase over basic, hydroxide ion-containing agents which are present, for example, in a column. In this process, 1 mol of carboxylic acid salt and 1 mol of water are formed per mol of carboxylic acid, so that the water consumed during the hydrolysis is replaced and the solution remains water-saturated. Basic agents which can be used are, for example, ion exchangers in the OH form, and alkali metal or alkaline earth metal hydroxides. After leaving the column, the solution no longer contains carboxylic acid formed in the enzymatic reaction, since this remains bound to the basic agents, but is again saturated with water by the formation of one mol of water per carboxylic acid salt. The reaction solution is continuously pumped over the hydrolase and then through the column containing the hydroxide ion-containing agents until the desired degree of conversion is achieved. For saturation with water, however, the organic reaction solution can also be passed through an aqueous phase after contact with the hydrolase or mixed with an aqueous phase and allowed to settle. A possible aqueous phase is pure water, a buffer solution or a salt solution. Preferably, the pH of the aqueous phase, which falls due to the introduction of the acid formed in the reaction, is kept approximately constant by addition of a base. The pH should neither fall below 3 nor rise above 11. Preferably, a pH range from 5 to 10, particularly preferably from 6 to 8, is maintained. Suitable bases for neutralization are the customary bases, for example alkali metal or alkaline earth metal hydroxides, carbonates and hydrogen carbonates, or $NH_4OH$ etc., alkali metal hydroxides such as potassium hydroxide or sodium hydroxide preferably being employed. The base is added as an aqueous solution, preferably in combination with a pH-measuring system, for example a hydrogen electrode, preferably in automated form. As a result of addition of the base, the carboxylic acid forms a salt with the base added, which remains in the aqueous phase so that the carboxylic acid formed is removed from the hydrolysis equilibrium, while the organic solution separates from the aqueous phase because of its low miscibility and during the course of this is saturated with water. The water-saturated organic solution is then again passed over the hydrolase. This procedure is continued until the desired degree of conversion is achieved. The reaction is then discontinued and the reaction products are isolated and optionally purified.

The carboxylic acid formed in the course of the process, which is isolated as the salt as described above, can be obtained in the customary manner by acidification and, if appropriate, extraction and purified by distillation, chromatography or recrystallization.

If the carboxylic acid formed in the course of the process is not the desired product, but the second hydrolysis product, i.e., for example the alcohol, the amine or the thiol, or if both carboxylic acid and the alcohol, the amine or the thiol are the desired product, or if no base is added during the saturation of the organic reaction solution with water, the desired products are obtained and/or purified from the organic reaction solution after discontinuation of the reaction in a customary manner, for example by extraction, distillation, crystallization and recrystallization or chromatography.

It has unexpectedly been shown that the enzyme activity can be considerably raised by washing the hydrolase with chloroform after a reaction cycle and before the subsequent reaction cycle, if chloroform has not been employed as organic solvent for the carboxylic acid derivative. Thus, the specific activity of a lipase altogether rose during the course of some reaction cycles from 138 to 339 mmol per hour per gram of lipase, after which the activity of the lipase remained approximately constant.

The process is expediently carried out at a temperature at which the hydrolase exhibits the highest activity. The temperatures here are in general between 0° and 40° C., preferably between 20° and 30° C., particularly preferably at room temperature, and in specific cases even higher, but in any case below the boiling point of the solvent and below the deactivation temperature of the hydrolase used.

The process can be carried out continuously or batchwise and is preferably carried out continuously.

In the case of the use of chiral or prochiral carboxylic acid derivatives, if the enantiomeric excess of an enantiomer in the product obtained, which is formed in the reaction with the hydrolase, is not sufficient because of a low stereospecificity of the hydrolase, the product obtained after one reaction cycle can be converted into a carboxylic acid derivative again and employed in the process according to the invention, a further enrichment of the desired enantiomer of the product being achieved. Sometimes, it is also expedient for achieving a higher enantiomeric purity to discontinue the process even after small conversion rates.

In a particular embodiment of the process, an optically active carboxylic acid derivative, in particular an optically active carboxylic acid ester which has the chiral center in the acid moiety, the desired product mainly being an enantiomer of an optically active carboxylic acid, is dissolved in diisopropyl ether or toluene as concentrated as possible and saturated with water in a storage container into which an aqueous phase has been introduced by mixing with the aqueous phase with stirring. With the aid of a pump, the water-saturated organic phase is passed from the storage container over a lipase which, absorbed on an inert support outside the storage container, is expediently introduced into a column so that the lipase does not come into contact with the aqueous phase from the storage container. During the course of this, the hydrolysis takes place to an enzyme-specific extent. The organic reaction solution is then fed back into the aqueous phase of the storage container. The pH of the aqueous phase, which falls due to the introduction of the carboxylic acid formed, is kept approximately at pH 7 by addition of an aqueous sodium hydroxide or potassium hydroxide solution. As a result, the carboxylic acid forms a salt and remains in the aqueous solution. The liberated alcohol and the unreacted starting compound remain dissolved in the organic reaction solution which, because of its low miscibility with water, separates from the aqueous phase of the storage container and is passed over the hydrolase again and then over the aqueous phase again in a circulation process until the desired degree of conversion is achieved. The reaction is then discontinued and the aqueous phase separated from the organic phase. To isolate the carboxylic acid formed, the aqueous phase is acidified in the customary manner and the liberated carboxylic acid is extracted. Purification by recrystallization, distillation or chromatography can be added, it being perfectly possible to achieve a further enrichment of the desired enantiomer.

In a particularly preferred embodiment of the process according to the invention, distilled water is introduced into a storage container and mixed with stirring with the solution of an enantiomeric mixture of a carboxylic acid ester which is substituted in the 2-position of the acid moiety, preferably by halogen, in diisopropyl ether and allowed to settle. The organic phase is then continuously passed back over a lipase which is present adsorbed on Celite packed in a column outside the storage container and then into the aqueous phase of the storage container, the pH of the aqueous phase being kept constant in a range from 6 to 9 by addition of an aqueous alkali metal hydroxide. The aqueous phase can be removed from the storage container during the course of this and replaced by addition of fresh aqueous phase. The organic phase, which mainly contains the enantiomer of the chiral carboxylic acid ester not used by the enzyme and the alcohol formed, can also be removed from the storage container after achieving the desired degree of conversion and replaced by fresh organic phase. The recovery of the pure or enriched enantiomers of the optically active carboxylic acid from the aqueous solution is carried out by acidification and extraction of the aqueous solution with an organic solvent for the carboxylic acid.

With the aid of the process according to the invention, a carboxylic acid derivative is enzymatically hydrolyzed in a simple manner in an organic solvent and the desired product is isolated in a simple manner, it being possible to introduce the enzyme in non-immobilized form and it being possible, in particular, to convert an enantiomeric mixture of a chiral starting compound into a highly enriched enantiomer of an optically active compound, if appropriate by using several reaction cycles, the solvent being used again and again, virtually no loss of enzyme or loss of activity of the enzyme occurring over long periods and no environmentally harmful waste products being formed and having to be processed again or disposed of. The process thus represents an enrichment of the art.

EXAMPLE 1

20.05 g of an enantiomeric mixture of 5.61 g of 2-ethylhexyl S-2-bromopropionate and 14.44 g of 2-ethylhexyl R-2-bromopropionate, which corresponds to an enantiomeric excess of the R-enantiomer of 44%, prepared by esterification of a corresponding enantiomeric mixture of 2-bromopropionic acid with 2-ethylhexanol, were dissolved using diisopropyl ether so that 170 ml of solution resulted. The solution was introduced into and stirred in 140 ml of water which had been mixed with 5.5 ml of ethanol and introduced into a container. During the course of this, 2 phases formed. The water-saturated organic phase was then pumped over 1.5 g of a *Candida cylindracea* lipase, which was introduced mixed with 12 g of Celite packed in a column outside the container, at an approximate pump velocity of 100 ml/min. After passage through the column, the organic reaction solution was passed into the aqueous phase of the container. The pH of the aqueous phase was automatically kept at 5 to 8 by addition of aqueous 2M sodium hydroxide. By this means, the sodium salt of the 2-bromopropionic acid resulting in the reaction was formed, which remained in the aqueous solution, while the organic reaction solution was saturated with water and separated from the aqueous phase of the container. The organic solution, now saturated with water again, was again continuously pumped over the lipase and then through the aqueous phase. After 0.5 hours, 2.05 ml, and after 1.5 hours, 5.85 ml of 2M aqueous sodium hydroxide were consumed in this process and a degree of conversion of 15% was achieved. The aqueous solution was then acidified with sulfuric acid, and the 2-bromopropionic acid liberated by this means was extracted with the aid of diisopropyl ether and isolated by evaporation of the extracting agent. In this way, 1.65 g of an enantiomeric mixture of R- and S-2-bromopropionic acid having an optical rotation $(alpha)_D^{20}$ of +25.4° were obtained, which corresponds to an enantiomeric excess of 90.4% of the R-enantiomer, i.e. 0.08 g of S- and 1.57 g of R-2-bromopropionic acid had been formed. The specific activity of the lipase was 5.2 mmol per hour per gram of lipase.

EXAMPLES 2 to 10

Examples 2 to 7 were carried out in the same manner as described in Example 1, using the same *Candida cylindracea* lipase of Example 1, the reaction time extending to about 4 hours and the reaction being discontinued on achieving a degree of conversion of about 44%. The column containing the *Candida cylindracea* lipase was washed with diisopropyl ether after each reaction cycle. Examples 8 to 10 were carried out in the same manner as described in Example 1, but using a 6-fold amount of 2-ethylhexyl 2-bromopropionate, of diisopropyl ether, of water and of ethanol using the same *Candida cylindracea* lipase of Examples 1 to 7. The column containing the *Candida cylindracea* lipase was washed with diisopropyl ether after each reaction cycle. In this case, the results which are summarized in Tables 1 and 2 were obtained.

TABLE 1

| h | \multicolumn{9}{c}{Examples} |
| | 2 | 3 | 4 | 5 | 6 | 7 | 8 | 9 | 10 |
| | \multicolumn{9}{c}{Percent conversion after hours} |
| --- | --- | --- | --- | --- | --- | --- | --- | --- | --- |
| 0.5 | 7.3 | | | 6.3 | | 7.1 | 5.8 | 3.3 | 2.2 | 1.8 |
| 1.0 | 13.8 | | | | | 14.6 | | | | |
| 1.5 | | 19.6 | 20.4 | 20.5 | | | | | |
| 2.0 | | 24.9 | | 26.2 | 29.1 | | | | |
| 2.5 | 29.9 | 29.9 | 32.0 | 30.4 | 34.9 | 27.5 | 7.3 | 5.3 | |
| 3.0 | | 34.7 | | | 39.4 | | | | |
| 3.5 | 38.9 | | | | | | | | |
| 4.0 | 42.6 | | 46.6 | | | | | | |
| 4.2 | 43.9 | 43.9 | | | 44.2 | 43.9 | | | |
| 4.5 | | | | | | 43.9 | | | |
| 18.0 | | | | | | | | | 35.7 |
| 19.0 | | | | | | | | 37.7 | |
| 20.5 | | | | | | | 39.4 | | |
| 24.13 | | | | | | | 44.1 | | |
| 24.25 | | | | | | | | 44.1 | 44.1 |

TABLE 2

| Example | G (g) | alpha (°) | ee (%) | Act |
| --- | --- | --- | --- | --- |
| 2 | 4.66 | +27.1 | 96.4 | 5.3 |
| 3 | 4.67 | +26.2 | 93.2 | 5.3 |
| 4 | 4.91 | +26.4 | 94.0 | 5.9 |
| 5 | 4.66 | +28.2 | 100.4 | 5.3 |
| 6 | 4.68 | +25.7 | 91.5 | 5.4 |
| 7 | 4.60 | +28.6 | 101.3 | 4.9 |
| 8 | 28.0 | +27.3 | 97.2 | 5.5 |
| 9 | 27.7 | +27.7 | 98.6 | 5.5 |
| 10 | 28.03 | +28.5 | 101.0 | 5.5 |

The *Candida cylindracea* lipase of Example 1 was thus altogether employed for 95 hours without losing activity.

In the Tables
h: denotes reaction time (hours)
Percent conversion: denotes reacted proportion of the enantiomeric mixture of 2-ethylhexyl 2-bromopropionate
G(g): denotes yield in grams
alpha(°): denotes optical rotation $(alpha)_D^{20}$
ee(%): denotes enantiomeric excess of R-2-bromopropionic acid obtained compared with S-2-bromopropionic acid
Act: denotes specific activity of the *Candida cylindracea* lipase in mmol per hour per gram of lipase.

EXAMPLE 11

20 g of a racemic mixture of 2-ethylhexyl R- and S-2-bromopropionate were dissolved in 150 ml of diisopropyl ether. This solution was introduced and stirred in a container into which 70 ml of water had been introduced. 2 phases formed during the course of this. The organic water-saturated phase was then pumped over 50 mg of a *Candida cylindracea* lipase, mixed with 2.8 g of Celite, and introduced into a column outside the container, at an approximate pump velocity of 100 ml/min. After passage through the column, the organic reaction solution was treated as described in Example 1. After 6.22 hours, a degree of conversion of 29.17% was achieved and the reaction was discontinued. In this way, 4.3 g of an enantiomeric mixture of R- and S-2-bromopropionic acid having an optical rotation $(alpha)_D^{20}$ of +20.6° were obtained, which corresponds to an enantiomeric excess of the R-enantiomer of 73.3%.

The specific activity of the lipase was 70.78 mmol per hour per gram of lipase.

EXAMPLES 12-17

The examples were carried out as described in Example 11 using the same starting amounts, the column, which contained the same lipase as Example 11, having been washed with chloroform before each new passage. In this case, the results which are collated in Table 3 were obtained.

TABLE 3

| Ex. | Percent conversion | after time (in hours) | alpha (°) | ee (%) | Act. |
| --- | --- | --- | --- | --- | --- |
| 12 | 29.8 | 3.25 | +21.6 | 76.9 | 138.5 |
| 13 | 30 | 1.75 | +22.1 | 78.6 | 258.3 |
| 14 | 29.8 | 2.23 | +21.3 | 75.8 | 236.8 |
| 15 | 30 | 1.58 | +22.7 | 80.8 | 285.5 |
| 16 | 30 | 1.33 | +20.0 | 71.2 | 339.0 |
| 17 | 30 | 1.80 | +17.2 | 61.2 | 251.1 |

EXAMPLE 18

The example was carried out as described in Example 11 using 45.1 g of a racemic mixture of 2-ethylhexyl R- and S-2-bromopropionate and 50 mg of a *Candida cylindracea* lipase. In this case, a degree of conversion of 45% was achieved after 19.25 hours. 9.88 g of an enantiomeric mixture of R- and S-2-bromopropionic acid having an optical rotation $(alpha)_D^{20}$ of $+21.5°$, which corresponds to an enantiomeric excess of the R-enantiomer of 76.5%, were obtained.

EXAMPLE 19

The 2-bromopropionic acid obtained in Example 18 was chemically esterified with 2-ethylhexanol. The ester was reacted as described in Example 18 with a lipase described therein. In this case, a degree of conversion of 72.3% was achieved after 15.25 hours. In this way, 6.62 g of an enantiomeric mixture of R- and S-2-bromopropionic acid having an optical rotation $(alpha)_D^{20}$ of $+26.4°$, which corresponds to an enantiomeric excess of R-2-bromopropionic acid of 94%, were obtained.

EXAMPLES 20 to 25

Examples 20–21, 22–23 and 24–25 were carried out as Examples 18–19 in each case using the same amount of starting substances and respectively using the same *Candida cylindracea* lipase of Example 18. The results are summarized in Table 4.

TABLE 4

| Ex. | Reaction (%) | After time (h) | Yield (g) | alpha (°) | ee (%) |
|---|---|---|---|---|---|
| 20 | 53.6 | 17 | 12.6 | +18.7 | 66.5 |
| 21 | 63.7 | 22 | 8.0 | +26.2 | 93.2 |
| 22 | 42.6 | 22 | 11.1 | +17.8 | 63.3 |
| 23 | 62.9 | 26.75 | 6.7 | +26.2 | 93.2 |
| 24 | 43.2 | 25.5 | 11.5 | +15.9 | 56.6 |
| 25 | 57.2 | 19.5 | 6.5 | +27.2 | 96.8 |

EXAMPLE 26

41 g of a racemic mixture of butyl R- and S-2-chloropropionate were dissolved in 360 ml of diisopropyl ether and incorporated with stirring with 200 ml of water which had been introduced into a container. 2 phases formed during the course of this. The organic upper phase was pumped over 15 g of a *Geotrichum candidum* lipase, which was mixed with 60 g of Celite in a column attached outside the container, at a pump velocity of 100 ml/min. The organic reaction solution was then passed back into the aqueous phase of the container, which was kept at a pH between 6 and 8 with the aid of an automated pH-measuring device with the addition of aqueous 2M sodium hydroxide. By this means, the sodium salt of the 2-chloropropionic acid resulting in the reaction was formed, which remained in the aqueous phase. The organic reaction solution separated from the aqueous phase and was continuously pumped over the lipase and then again through the aqueous phase.

After 44.5 hours, a degree of conversion of 20.6% was achieved and the reaction was discontinued. The aqueous solution was acidified by addition of sulfuric acid and extracted with chloroform and the organic solvent was dried over sodium sulfate and evaporated.

In this way, 5.3 g of an enantiomeric mixture of R- and S-2-chloropropionic acid having an optical rotation $(alpha)_D^{20}$ of $-12°$ were obtained, which corresponds to an enantiomeric excess of the S-enantiomer of 73.2%.

EXAMPLE 27

55.5 g of a racemic mixture of 2-ethylhexyl R- and S-2-chloropropionate were dissolved in 360 ml of diisopropyl ether and introduced with stirring into a container into which 200 ml of water had been introduced. 2 phases were formed during the course of this. The organic, water-saturated upper phase was passed over 1 g of a *Candida cylindracea* lipase which was present packed in a column mixed with 10 g of Celite outside the container. The process as described in Example 1 was then carried out. After achieving a degree of conversion of 32%, the reaction was discontinued. In this way, an enantiomeric mixture of R- and S-2-chloropropionic acid having an optical rotation $(alpha)_D^{20}$ of $+6.9°$ was obtained, which corresponds to an enantiomeric excess of the R-enantiomer of 42.1%. The specific activity of the lipase was 11.58 mmol per hour per gram of lipase.

EXAMPLE 28

55.5 g of a racemic mixture of 2-ethylhexyl R- and S-2-chloropropionate were dissolved in 360 ml of diisopropyl ether and introduced with stirring into a container into which 200 ml of water had been introduced. 2 phases were formed during the course of this. The organic, water-saturated upper phase was pumped at a pump velocity of 100 ml/min over a column which contained 2 g of a *Candida cylindracea* lipase which had been cross-linked by stirring with 2 ml of 50% glutaraldehyde in diisopropyl ether and mixed with 13 g of Celite. The procedure as described in Example 1 was then carried out. After achieving a degree of conversion of 32%, the reaction was discontinued. In this way, an enantiomeric mixture of R- and S-2-chloropropionic acid having a rotation $(alpha)_D^{20}$ of $+7.3°$ was obtained, which corresponds to an enantiomeric excess of the R-enantiomer of 44.5%. The specific activity of the lipase was 4.8 mmol per hour per gram of lipase.

EXAMPLE 29

Using 55.2 g of a racemic enantiomer mixture of 2-ethylhexyl 2-chloropropionate, 400 ml of hexane instead of diisopropyl ether and 3 g of a *Candida cylindracea* lipase, mixed with 21 g of Celite, a degree of conversion of 78.6% was achieved in the manner described in Example 26 after 19 hours. In this way, an enantiomeric mixture of R- and S-2-chloropropionic acid having an optical rotation $(alpha)_D^{20}$ of $+2.5°$ was obtained, which corresponds to an enantiomeric excess of the R-enantiomer of 15.2%. The enantiomeric excess of the S-enantiomer in the unreacted ester was 56%.

EXAMPLE 30

Using 294.1 g of a racemic enantiomeric mixture of 2-ethylhexyl 2-chloropropionate, 100 ml of diisopropyl ether and 20 ml of acetone instead of pure diisopropyl ether and 10 g of *Candida cylindracea* lipase, mixed with 50 g of Celite, the procedure was carried out in the manner described in Example 26 up to a degree of conversion of 57%. In this way, an enantiomeric mixture of R- and S-2-chloropropionic acid having an optical rotation $(alpha)_D^{20}$ of $+6.1°$ was obtained, which corresponds to an enantiomeric excess of the R-enantiomer of 37%.

EXAMPLE 31

Using 57.2 g of a racemic enantiomeric mixture of phenylethyl R- and S-2-chloropropionate, dissolved in 400 ml of diisopropyl ether, and 3 g of a *Candida cylindracea* lipase, mixed with 15 g of Celite, a degree of conversion of 60% was achieved in the manner described in Example 26 after 1.30 hours. In this way, an enantiomeric mixture of R- and S-2-chloropropionic acid having an optical rotation (alpha)$_D^{20}$ of +6.1° was obtained, which corresponds to an enantiomeric excess of the R-enantiomer of 37%. The specific activity of the lipase was 41.7 mmol per hour per gram of lipase.

EXAMPLE 32

The reaction was carried out as Example 31 using 159 g of a racemic enantiomeric mixture of phenylethyl R-and S-2-chloropropionate as starting material, dissolved in 400 ml of diisopropyl ether, and the same lipase used in Example 31, which had been washed with diisopropyl ether. After 4.12 hours, a degree of conversion of 67% was achieved and the reaction was discontinued. In this way, an enantiomeric mixture of R- and S-2-chloropropionic acid having an optical rotation (alpha)$_D^{20}$ of +5.3° was obtained, which corresponds to an enantiomeric excess of the R-enantiomer of 32.3%. The specific activity of the lipase was 40.8 mmol per hour per gram of lipase.

EXAMPLE 33 to 35

41 g of a racemic enantiomeric mixture of butyl 2-chloropropionate were dissolved in 360 ml of solvent and introduced with stirring into a container into which 200 ml of water had been introduced. 2 phases were formed during the course of this. The organic, water-saturated phase was pumped through a column which contained 3 g of a *Candida cylindracea* lipase, mixed with 9 g of Celite, up to a degree of conversion of 33%. The procedure described in Example 1 was then carried out. In this way, the following results were obtained:

| Example | Solvent | Act | alpha |
|---|---|---|---|
| 33 | diisopropyl ether | 27.18 | +5.4 |
| 34 | n-heptane | 12.78 | +5.2 |
| 35 | chloroform | 2.17 | +5.6 |

Act: specific activity in mmol per hour per gram of lipase
alpha: optical rotation (alpha)$_D^{20}$

EXAMPLE 36

55.2 g of a racemic mixture of 2-ethylhexyl 2-chloropropionate were dissolved in 400 ml of diisopropyl ether and introduced with stirring into a container into which 200 ml of water had been introduced. 2 phases formed during the course of this. The organic, water-saturated phase was passed over 6 g of a *Humicola lanuginosa* lipase mixed with 20 g of Celite. The procedure was then continued as described in Example 1. After 25 hours, a degree of conversion of 32.4% was achieved and the reaction was discontinued.

In this way, an enantiomeric mixture of R- and S-2-chloropropionic acid having an optical rotation (alpha)$_D^{20}$ of +8.9° was obtained, which corresponds to an enantiomeric excess of the R-enantiomer of 54.3%. The specific activity of the lipase was 0.54 mmol per hour per gram of lipase.

EXAMPLE 37

The reaction was repeated as Example 36 using the same starting materials and amounts and using the same lipase employed in Example 36 after washing the enzyme-containing column with diisopropyl ether. After 48 hours, a degree of conversion of 64.8% was achieved and the reaction was discontinued. In this way, an enantiomeric mixture of R- and S-2-chloropropionic acid having an optical rotation (alpha)$_D^{20}$ of +4.7° was obtained, which corresponds to an enantiomeric excess of the R-enantiomer of 28.7%. The specific activity of the lipase was 0.56 mmol per hour per gram of lipase.

EXAMPLE 38

Using the organic phase from Example 37, which contained 19.4 g of 2-ethylhexyl 2-chloropropionate, and a *Pseudomonas fluorescens* lipase which was mixed with 12.5 g of Celite, a conversion of 35.8% was achieved after 8.6 hours in the manner described in Example 36. In this way, an enantiomeric mixture of R- and S-2-chloropropionic acid having a rotation (alpha)$_D^{20}$ of −12.6° was obtained, which corresponds to an enantiomeric excess of the S-enantiomer of 76.8%. The activity of the lipase was 1.48 mmol per hour per gram of lipase.

EXAMPLE 39

Using 102.5 g of an enantiomeric mixture of 2-ethylhexyl R- and S-2-chloropropionate having an enantiomeric excess of the S-enantiomer of 58.5%, prepared by esterification of the corresponding 2-chloropropionic acid enantiomers with 2-ethylhexanol, and 4.8 mg of a *Chromabakterium viscosum* lipase mixed with 10 g of Celite, a degree of conversion of 22.5% was achieved in the manner described in Example 36. In this way, 4.7 g of an enantiomeric mixture of R- and S-2-chloropropionic acid having an optical rotation (alpha)$_D^{20}$ of −12.9° was obtained, which corresponds to an enantiomeric excess of the S-enantiomer of 78.7%. The specific activity of the lipase was 1.04 mol per hour per gram of lipase.

EXAMPLE 40

In the manner described in Example 27 but at 0°±1.5° C. using 6 g of a *Candida cylindracea* lipase which was mixed with 24 g of Celite, 57.6 g of a racemic enantiomeric mixture described in Example 27 was converted in the course of 5 hours with a degree of conversion of 70% to an enantiomeric mixture of R- and S-2-chloropropionic acid having an optical rotation (alpha)$_D^{20}$ of +4.3°, which corresponds to an enantiomeric excess of 26%. The specific activity of the lipase was 5.83 mmol per hour per gram of lipase.

EXAMPLE 41

In the manner described in Example 40, but at a temperature of 10° C., a degree of conversion of 70% was achieved in 2.8 hours. The specific activity of the lipase was 10.3 mmol per hour per gram of lipase. The optical rotation (alpha)$_D^{20}$ of the resulting enantiomeric mixture was 4.4°.

EXAMPLE 42

56.6 g of a racemic enantiomeric mixture of 2-ethylhexyl 2-chloropropionate were dissolved in 400 ml of water-saturated diisopropyl ether and introduced into a container. The solution was pumped over 3 g of a *Can-*

*dida cylindracea* lipase which was mixed with 15 g of Celite. The reaction solution formed in this process was then pumped through a column which contained 10 g of calcium hydroxide mixed with 20 g of Celite. In this way, the 2-chloropropionic acid formed in the reaction remained in the column owing to salt formation, while the water in the organic solution consumed during the hydrolysis was replaced again. The further reaction procedure was carried out continuously in the manner described above, until after 4 hours a degree of conversion of 34.3% was achieved. In this way, an enantiomeric mixture of R- and S-2-chloropropionic acid having an optical rotation (alpha)$_D^{20}$ of $+7.0°$ was obtained, which corresponds to an enantiomeric excess of the R-enantiomer of 43%.

EXAMPLE 43

6.59 g of a racemic enantiomeric mixture of butyl 2-chloropropionate were dissolved in 75 ml of diisopropyl ether and mixed with 1.6 ml of a sodium phosphate buffer (pH=7), 0.1 g of Sephadex G 50 from Pharmacia, preswollen in water, 6 g of Celite and 6 g of a *Geotrichum candidum* lipase and the mixture was stirred at room temperature. After 168.8 hours, a degree of conversion of 37.4% was achieved and the reaction was discontinued. In this way, an enantiomeric mixture of R- and S-2-chloropropionic acid having an optical rotation of (alpha)$_D^{20}$ of $-8.8°$ was obtained, which corresponds to an enantiomeric excess of the S-enantiomer of 53.7%.

EXAMPLE 44

As described in Example 43, but using 15 g of a racemic enantiomeric mixture of propyl 2-chloropropionate, 5 g of a *Geotrichum candidum* lipase, 5 g of Celite, 2.5 ml of a 10 mM sodium phosphate buffer (pH=7) and 340 mg of Hydrogel Evergreen 500, Chemie Linz AG, preswollen in water, a conversion of 24.5% was achieved after 118.5 hours. In this way, an enantiomeric mixture of R- and S-2-chloropropionic acid having an optical rotation (alpha)$_D^{20}$ of $+3.0°$ was obtained, which corresponds to an enantiomeric excess of the R-enantiomer of 18.3%.

EXAMPLE 45

In the manner described in Example 43, but using 0.1 g of Hydrogel Evergreen 500, Chemie Linz AG, preswollen in water, instead of Sephadex G 50, a degree of conversion of 24% was achieved after 46.8 hours. In this way, an enantiomeric mixture of R- and S-2-chloropropionic acid having an optical rotation (alpha)$_D^{20}$ of $-11.7°$ was obtained, which corresponds to an enantiomeric excess of the S-enantiomer of 71.3%.

EXAMPLE 46

6.58 g of a racemic enantiomeric mixture of butyl 2-chloropropionate were dissolved in 50 ml of diisopropyl ether and mixed with 1 g of Celite, 0.1 g of Sephadex G 50 from Pharmacia, preswollen in water, 0.8 g of 10 mM sodium phosphate buffer (pH=7) and 0.8 g of a *Candida cylindracea* lipase and the mixture was stirred at room temperature. After 1.75 hours, the degree of conversion was 34.5%. The reaction was discontinued and the hydrogel and the lipase were filtered off. The reaction solution contained an enantiomeric mixture of R- and S-2-chloropropionic acid having a rotation (alpha)$_D^{20}$ of $+4.3°$, which corresponds to an enantiomeric excess of the R-enantiomer of 26.2%. The specific activity of the lipase was 9.86 mmol per hour per gram of lipase.

The specific optical rotation of the products obtained (alpha)$_D^{20}$ indicated in the examples was in all examples measured at a wavelength of 589 nm (sodium D line), 20° C., c=1 in chloroform. The Celite employed in the examples was "Celite Hyflo Super-Cel" from Fluka, particle size 2 to 25 μ.

EXAMPLES 47–52

In each case, 7.0 g of a racemic enantiomeric mixture of 1-phenylethyl R- and S-octanoate were dissolved in 300 ml of diisopropyl ether and introduced with stirring into a container into which 200 ml of water had been introduced. 2 phases formed during the course of this. As described in Example 1, the organic, water-saturated phase was pumped through a column which contained 3 g of *Candida cylindracea* lipase from Meito, mixed with 22 g of Celite, the same lipase being used for all of Examples 47 to 52. As described in Example 1, the pH of the aqueous phase was kept at 5 to 8. After achieving a degree of conversion of about 30%, the aqueous phase was extracted with diisopropyl ether and the reaction was discontinued. After evaporation of the diisopropyl ether, 1-phenyl-ethanol was isolated from the residue which remained with the aid of vacuum distillation. In this way, the results summarized in Table 5 were obtained.

TABLE 5

| Ex. | Percent conversion | after time (in hours) | alpha (°) | ee (%) | Act |
|---|---|---|---|---|---|
| 47 | 32 | 22.0 | 41.2 | 92 | 0.137 |
| 48 | 30 | 22.0 | — | — | 0.128 |
| 49 | 31 | 23.0 | 41.2 | 92 | 0.127 |
| 50 | 26 | 20.5 | — | — | 0.119 |
| 51 | 29 | 24.5 | — | — | 0.111 |
| 52 | 29 | 26.5 | 39.7 | 88 | 0.103 |

Act: specific activity of the *Candida cylindracea* lipase in mmol per hour per gram of lipase
alpha: optical rotation, measured at a wavelength of 589 nm, 20° C., c = 1 in methanol
ee enantiomeric excess of the R- to the S-1-phenylethanol obtained
— the reaction solution was not worked up

What we claim is:

1. Process for the enzymatic hydrolysis of a carboxylic acid derivative selected from the group consisting of carboxylic acid esters, diesters, triesters, carboxylic acid amides, carboxylic acid thioesters and thiocarboxylic acid analogs thereof, comprising (a) dissolving the carboxylic acid derivative in an organic solvent which is miscible with water only to a slight extent, (b) saturating the solution with water and bringing it into contact with a hydrolase, hydrolysis taking place with consumption of water, and (c) continuously saturating the organic reaction solution with water and bringing it into contact with the hydrolase until the desired degree of conversion is achieved.

2. Process according to claim 1, comprising the saturation of the organic phase with water being carried out with the aid of a water-containing hydrogel.

3. Process according to claim 1, comprising the saturation with water being carried out after the hydrolysis by passing the organic reaction solution over hydroxide ion-containing agents, the carboxylic acid formed thus being removed from the reaction equilibrium and the water consumed during the hydrolysis being replaced.

4. Process according to claim 1, comprising the carboxylic acid derivative being dissolved in the organic solvent and the organic solution formed being introduced into an aqueous phase of a storage container, the organic solution thereby being saturated with water and being separated from the aqueous phase, pumping this water-saturated organic solution through a reaction vessel which contains the hydrolase, pumping back the organic reaction solution thus formed into the aqueous phase of the storage container, whose pH being kept constant by addition of a base, thereby the carboxylic acid formed remains in the aqueous phase as the salt of the base added, thus the carboxylic acid being removed from the hydrolysis equilibrium, while the organic phase being saturated again with water and separated from the aqueous phase and continuing pumping the organic phase over the hydrolase and subsequently into the aqueous phase until the desired degree of conversion is achieved.

5. Process according to claim 4, comprising washing the hydrolase after completion of a reaction cycle, with chloroform before employing it in a new reaction cycle.

6. Process according to claim 1, comprising employing a chiral or prochiral carboxylic acid derivative selected from the group consisting of carboxylic acid esters, diesters, triesters, carboxylic acid amides, carboxylic acid thioesters and thiocarboxylic acid analogs thereof.

7. Process according to claim 1, comprising employing an enantiomeric mixture of a halopropionic acid ester.

8. Process according to claim 1, comprising employing an ether as the organic solvent.

9. Process according to claim 1, comprising employing a lipase as the hydrolase.

10. Process according to claim 1, comprising employing the hydrolase adsorbed on a support.

11. A process for the enzymatic hydrolysis of a carboxylic acid ester, comprising (a) dissolving the carboxylic acid ester in an ether with or without a ketone as co-solvent in an amount such that the ether does not become miscible with water, (b) saturating the solution formed with water and bringing it into contact with an esterase, hydrolysis taking place with consumption of water, and (c) continuously saturation of the organic solution with water and bringing it into contact with the esterase until the desired degree of conversion is achieved.

* * * * *